United States Patent
Su et al.

(10) Patent No.: US 11,452,703 B2
(45) Date of Patent: Sep. 27, 2022

(54) METHODS AND COMPOSITIONS FOR REDUCING ADIPOCYTE NUMBERS

(71) Applicant: Peregrine Ophthalmic PTE LTD., Singapore (SG)

(72) Inventors: Shih-Horng Su, Irvine, CA (US); Tina Howden, Singapore (SG)

(73) Assignee: Peregrine Ophthalmic PTE LTD., Singapore (SG)

( * ) Notice: Subject to any disclaimer, the term of this patent is extended or adjusted under 35 U.S.C. 154(b) by 184 days.

(21) Appl. No.: 16/880,531

(22) Filed: May 21, 2020

(65) Prior Publication Data
US 2021/0361609 A1 Nov. 25, 2021

(51) Int. Cl.
*A61K 31/216* (2006.01)
*A61P 43/00* (2006.01)
*A61K 47/54* (2017.01)
*A61K 9/127* (2006.01)

(52) U.S. Cl.
CPC ............ *A61K 31/216* (2013.01); *A61K 9/127* (2013.01); *A61K 47/544* (2017.08); *A61P 43/00* (2018.01)

(58) Field of Classification Search
CPC .... A61K 31/216; A61K 47/544; A61K 9/127; A61K 9/0014; A61K 9/0019; A61K 9/0048; A61K 9/0053; A61P 43/00
See application file for complete search history.

(56) References Cited

U.S. PATENT DOCUMENTS

| | | |
|---|---|---|
| 7,666,912 B2 | 2/2010 | Grosskreutz et al. |
| 8,829,050 B2 | 9/2014 | Grosskreutz et al. |
| 9,421,215 B2 | 8/2016 | Grosskreutz et al. |
| 9,795,614 B2 | 10/2017 | Grosskreutz et al. |
| 9,795,615 B2 | 10/2017 | Poloso et al. |
| 2005/0261373 A1 | 11/2005 | Ueno |
| 2015/0105462 A1 | 4/2015 | Singer et al. |
| 2015/0190359 A1 | 7/2015 | Venkatraman et al. |
| 2015/0250891 A1 | 9/2015 | Venkatraman et al. |
| 2016/0339039 A1 | 11/2016 | Whitcup et al. |

FOREIGN PATENT DOCUMENTS

| | | | | |
|---|---|---|---|---|
| WO | WO-2007111806 A2 | * | 10/2007 | ......... A61K 31/5575 |
| WO | WO2014/138426 A2 | | 9/2014 | |
| WO | WO-2015200425 A1 | * | 12/2015 | ......... A61K 31/5575 |

OTHER PUBLICATIONS

Bonfiglioli et al "Influence of Two Non-Steroidal Anti-Inflammatory Drugs on Lipolysis and on Plasma Post-Heparin Lipoprotein Lipase Activity in Normal Man" European Journal of Clinical Pharmacology vol. 20, pp. 263-267, 1981.
Choi et al "The Effect of Prostaglandin Analogue Bimatoprost on Thyroid-Associated Orbitopathy" Investigative Ophthalmology and Visual Science vol. 59, pp. 5912-5923, 2018.
Chusyd et al "Relationships Between Rodent White Adipose Fat Pads and Human White Adipose Fat Depots" Frontiers in Nutrition vol. 3, pp. 1-12, 2016.
Eftekhari et al "In Vivo Effects of Retrobulbar Bimatoprost Injection on Orbital Fat" Ophthalmic Plastic and Reconstructive Surgery vol. 34, pp. 201-204, 2018.
Flint et al "Regulation of Adipocyte Insulin Receptor Number and Metabolism During Late-Pregnancy" Molecular and Cellular Endocrinology vol. 20, pp. 101-111, 1980.
Lambert et al "Relationship Between Prostaglandin Biosynthesis and the Effect of Insulin on Hormone-Stimulated Lipolysis in Rat Adipose Tissue" Biochimica et Biophysica Acta vol. 431, pp. 132-138, 1976.
Lepak et al "Inhibition of Adipose Differentiation by 9 Alpha, 11 Beta-Prostaglandin F2 Alpha" Prostaglandins vol. 46, pp. 511-517, 1993.
Lepak et al "Prostaglandin F2 Alpha Stimulates Transforming Growth Factor-Alpha Expression in Adipocyte Precursors" Endocrinology vol. 136, pp. 3222-3229, 1995.
Li et al "Upper Airway Fat Tissue Distribution in Subjects with Obstructive Sleep Apnea and its Effect on Retropalatal Mechanical Loads" Respiratory Care vol. 57, pp. 1098-1105, 2012.
McCune et al "Comparative Studies on Fatty Acid Synthesis, Glycogen Metabolism, and Gluconeogenesis by Hepatocytes Isolated from Lean and Obese Zucker Rats" Metabolism vol. 30, pp. 1170-1178, 1981.
Miller et al "The Mechanism of Inhibition of 3T3-L1 Preadipocyte Differentiation by Prostaglandin F2Alpha" Endocrinology vol. 137, pp. 5641-5650, 1996.
Park et al "Changes to Upper Eyelid Orbital Fat from Use of Topical Bimatoprost, Travoprost, and Latanoprost" Japanese Journal of Ophthalmology vol. 55, pp. 22-27, 2011.
Reginato et al "Prostaglandins Promote and Block Adipogenesis Through Opposing Effects on Peroxisome Proliferator-Activated Receptor Y" The Journal of Biological Chemistry vol. 273, pp. 1855-1858, 1998.
Serrero et al "Prostaglandin $F_{2\alpha}$ Inhibits Epidermal Growth Factor Binding to Cellular Receptors on Adipocyte Precursors in Primary Culture" Biochemical and Biophysical Research Communications vol. 212, pp. 1125-1132, 1995.
Spooner et al. "Regulation of Mammary and Adipose Tissue Lipoprotein Lipase and Blood Triacylglycerol in Rats During Late Pregnancy" The Journal of Clinical Investigation vol. 60, pp. 702-708, 1977.

\* cited by examiner

*Primary Examiner* — Sarah Pihonak (57) ABSTRACT

A method for reducing a subcutaneous fat deposit or a visceral fat deposit in vivo by contacting the fat deposit with a composition of latanoprost encapsulated in a liposome formed solely of egg phosphatidylcholine (EggPC) or palmitoyloleoyl phosphatidylcholine (POPC). Also disclosed are methods for treating steatoblepharon, proptosis, and obstructive sleep apnea associated with excess upper airway fat by injecting into the eyelid, intraconal space, and upper airway fat deposit, respectively, the composition of latanoprost encapsulated in an EggPC or POPC liposome.

27 Claims, 9 Drawing Sheets
(8 of 9 Drawing Sheet(s) Filed in Color)

Fig. 4A control

Fig. 4B eggPC-Latanoprost

Fig. 4C POPC-Latanoprost

Fig. 4D Latanoprost

Fig. 4E DCA

Fig. 4F Control

METHODS AND COMPOSITIONS FOR REDUCING ADIPOCYTE NUMBERS

BACKGROUND

Several medical conditions exist in which it is desirable to reduce the amount of fat at an anatomical location.

Steatoblepharon is anterior prolapse of the eyelid fat pad, often referred to as an eyelid bag, resulting in a puffy appearance of the eyes. This condition is treated by surgery, i.e., blepharoplasty, to remove fat deposits from the eyelids. The surgery can have side-effects such as infection, bleeding, dry irritated eyes, difficulty closing eyes, noticeable scarring, injury to eye muscles, skin discoloration, the need for a follow-up surgery, temporarily blurred vision, and, in rare cases, loss of eyesight.

Proptosis, defined as the forward movement of the eye relative to its normal position in the eye socket, is a more serious condition. The most common cause of is proptosis is thyroid eye disease, in which abnormal thyroid function causes swelling of the muscles, fat, and other tissues around the eye, if not controlled, proptosis can result in failure of the eyelids to close properly when blinking and sleeping, leading to corneal damage. The swelling of tissues, including fat deposits, around the eye may prevent it from working well, which affects eye position and eye movements leading to double vision. In severe cases, the inflammation and enlargement of the tissues, muscles, and fat deposits behind the eye compresses the optic nerve, resulting in vision loss.

Proptosis can be treated by orbital decompression surgery. The risks associated with this surgery include diplopia, epiphora, nasolacrimal duct obstruction, scarring, bleeding in the nose or around the eye, eye or sinus infection, vision loss, optic nerve injury, cerebrospinal fluid leakage, eyelid malposition, pain or numbness around the eyes, scratching of the cornea, and swelling of the conjunctiva.

An alternative proptosis treatment is intravenous infusion of Teprotumumab (TEPEZZA™). Side effects include muscle cramps or spasms, nausea, hair loss, diarrhea, feeling tired, high blood sugar, hearing problems, taste changes, headache, and dry skin. Teprotumumab may also worsen existing inflammatory bowel disease, such as Crohn's disease or ulcerative colitis symptoms.

Further, there is no specific treatment for obstructive sleep apnea associated with excess upper airway fat deposits. In obese patients, bariatric surgery is often performed. Although the surgery might improve obstructive sleep apnea, it comes with the typical risks associated with any surgery.

There is a need to develop treatments for conditions such as steatoblepharon, proptosis, and obstructive sleep apnea that remove excess fat deposits without the side-effects of existing methods.

SUMMARY

To meet the above need, a method for reducing a subcutaneous fat deposit or a visceral fat deposit in vivo is provided. The method is carried out by contacting the fat deposit with an effective amount of a composition of latanoprost encapsulated in a liposome. The liposome is formed solely of egg phosphatidylcholine (EggPC) or palmitoyloleoyl phosphatidylcholine (POPC), and the effective amount of the is composition reduces the number of adipocytes in the fat deposit by 5% to 90%.

A similar method is provided for treating steatoblepharon in a subject by injecting into a fat deposit in an eyelid of the subject a composition of latanoprost encapsulated in an EggPC or POPC liposome. The composition reduces the number of adipocytes in the fat deposit by 5% to 90%.

Disclosed as well is a method for treating proptosis by injecting into the intraconal space of an eye of the subject the above-mentioned composition of latanoprost encapsulated in an EggPC or POPC liposome. Carrying out this method results in a reduction of adipocyte numbers in the intraconal space by at least 35%.

Further, provided is a method for treating obstructive sleep apnea associated with excess upper airway fat. This method is accomplished by injecting into an upper airway fat deposit an effective amount of a composition of latanoprost encapsulated in an EggPC or POPC liposome, thereby reducing the number of adipocytes in the upper airway fat deposit by 5% to 90%.

The details of several embodiments of the present invention are set forth in both the description and the drawings below. Other features, objects, and advantages of the invention will be apparent from the description and also from the appended claims. Finally, all references cited herein are hereby incorporated by reference in their entirety.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description below refers to the accompanying drawings, of which.

DETAILED DESCRIPTION

As summarized above, a method is provided for reducing a fat deposit, e.g., a subcutaneous fat deposit or a visceral fat deposit, in vivo. The method is carried out by contacting the fat deposit with a composition of latanoprost encapsulated in a liposome. The contacting step can be accomplished by direct injection of the composition into the fat deposit. Alternatively, the composition can be injected into an interstitial space adjacent to the fat deposit. In a particular method, the fat deposit is a subcutaneous fat deposit and the composition is injected subcutaneously into or adjacent to the subcutaneous fat deposit. Topical application of the composition to skin overlying the fat deposit is also within the scope of the invention.

The composition used in the above method includes latanoprost encapsulated in a liposome formed solely of EggPC or POPC. In other words, the liposome is free of any other components, e.g., lipids and sterols. The latanoprost-loaded EggPC and POPC liposomes can be those described in U.S. Pat. Nos. 10,272,040 and 9,956,195, respectively. The composition can be prepared also as described in these two US patents.

The concentration of latanoprost in the composition can range from 0.5 mg/mL to 3.0 mg/mL (e.g., 0.5, 1.0, 1.5, 2.0, 2.5, and 3.0 mg/mL). In one exemplary range, the concentration of latanoprost is 1.0 mg/mL to 2.3 mg/mL (e.g., 1.0, 1.1, 1.2, 1.3, 1.4, 1.5, 1.6, 1.7, 1.8, 1.9, 2.0, 2.1, 2.2, and 2.3 mg/mL).

The amount of composition necessary to reduce the adipocyte number varies according to the size of the fat deposit. In a particular method, a volume of 25 µL to 75 µl of the above-described composition is injected for each 0.5 cm$^3$ to 1.0 cm$^3$ of the fat deposit.

The amount of composition applied to the fat deposit in the above method is effective to reduce the number of adipocytes by 5% to 90% (e.g., 5%, 10%, 15%, 20%, 25%, 30%, 35%, 40%, 45%, 50%, 55%, 60%, 65%, 70%, 75%, 80%, 85%, and 90%). The reduction in adipocyte number can fall in the range of 10% to 90% or 35% to 90%.

Set forth in the Summary section is a method for treating a steatoblepharon by injecting the above-described liposomal latanoprost composition into a fat deposit in the eyelid of a subject. Injection of the composition reduces the number of adipocytes in the fat deposit by 5% to 90% (e.g., 5%, 10%, 15%, 20%, 25%, 30%, 35%, 40%, 45%, 50%, 55%, 60%, 65%, 70%, 75%, 80%, 85%, and 90%), as in the method described above. The latanoprost composition and its concentration is also the same as those described for the above fat-reducing method. For example, the concentration of latanoprost in the composition ranges from 0.5 mg/mL to 3.0 mg/mL and a volume of 25 µL to 75 µl of the composition is injected for each 0.5 cm$^3$ to 1.0 cm$^3$ of the fat deposit.

To repeat from above, a method for treating proptosis is also provided. The method features injecting into the intraconal space of an eye of a subject the above-mentioned composition of latanoprost encapsulated in an EggPC or POPC liposome.

In an example of this method, the proptosis is a result of thyroid-associated orbitopathy. In another example, the subject having proptosis suffers from Grave's disease or Hashimoto's thyroiditis.

In the method for treating proptosis, the latanoprost concentration in the injected composition ranges from 0.5 mg/mL to 3.0 mg/mL (e.g., 1.0 mg/mL to 2.3 mg/mL). The injection results in a reduction of adipocyte numbers in the intraconal space by at least 35% and as high as 90% (e.g., 35%, 40%, 45%, 50%, 55%, 60%, 65%, 70%, 75%, 80%, 85%, and 90%).

Finally, the method mentioned above for treating obstructive sleep apnea associated with an upper airway fat deposit is carried out by injecting into the upper airway fat deposit a composition of latanoprost encapsulated in an EggPC or POPC liposome having a latanoprost concentration of 0.5 mg/mL to 3.0 mg/mL (e.g., 1.0 mg/mL to 2.3 mg/mL).

Injection of the composition results in a reduction of adipocyte numbers in the upper airway fat deposit of 5% to 90% (e.g., 10% to 90% and 35% to 90%).

The upper airway fat deposit can be located in, but not limited to, the palate, the tongue, and the pharynx.

Without further elaboration, it is believed that one skilled in the art can, based on the disclosure herein, utilize the present disclosure to its fullest extent. The following specific examples are, therefore, to be construed as merely descriptive, and is not limitative of the remainder of the disclosure in any way whatsoever. All publications, including patent documents, cited herein are incorporated by reference in their entirety.

EXAMPLES

Example 1: Inhibition of Pre-Adipocyte Differentiation

Adipose-derived mesenchymal stem cells, i.e., pre-adipocytes, were cultured and differentiated into adipocytes following established protocols. Briefly, adipose derived mesenchymal stem cells were obtained from ATCC (PCS500011™, Manassas, Va.) and cultured in Mesenchymal Stem Cell Basal Medium (ATCC® PCS500030™) with Growth Kit (ATCC® PCS500040™) at 37° C. in 5% $CO_2$. To induce differentiation, ADMSC cultures were grown to 70% to 80% confluence and the medium replaced by adipogenic differentiation medium (StemPro® Adipogenesis Differentiation Kit; Gibco Life Technologies™, USA). The medium was changed twice weekly.

Figure 1A:
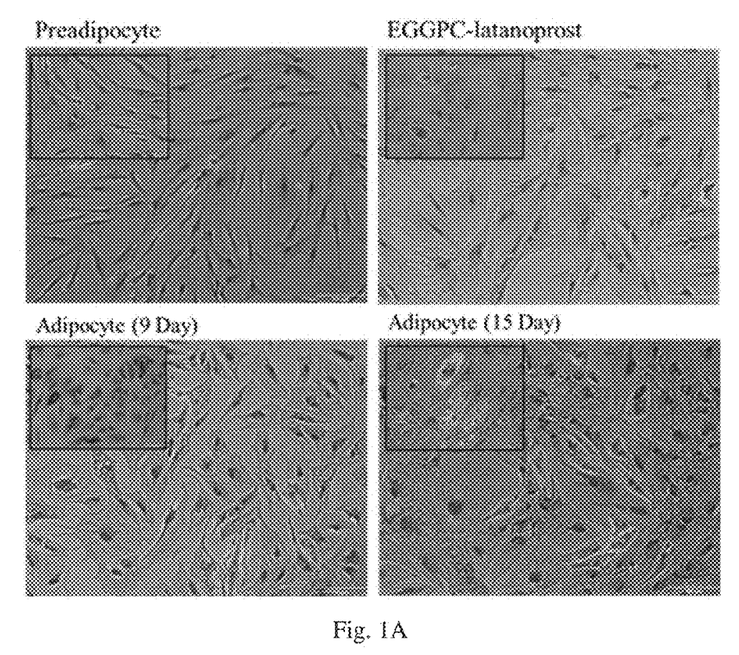
FIG. 1A shows light microscopy images of lipid staining with Oil red O (ORO) of preadipocytes, differentiated adipocytes, and differentiated adipocytes treated with an EggPC-latanoprost liposomal composition (LIPOLat-E). Neutral lipids stain red and nuclei stain blue. (200× magnification).
Figure 1B:
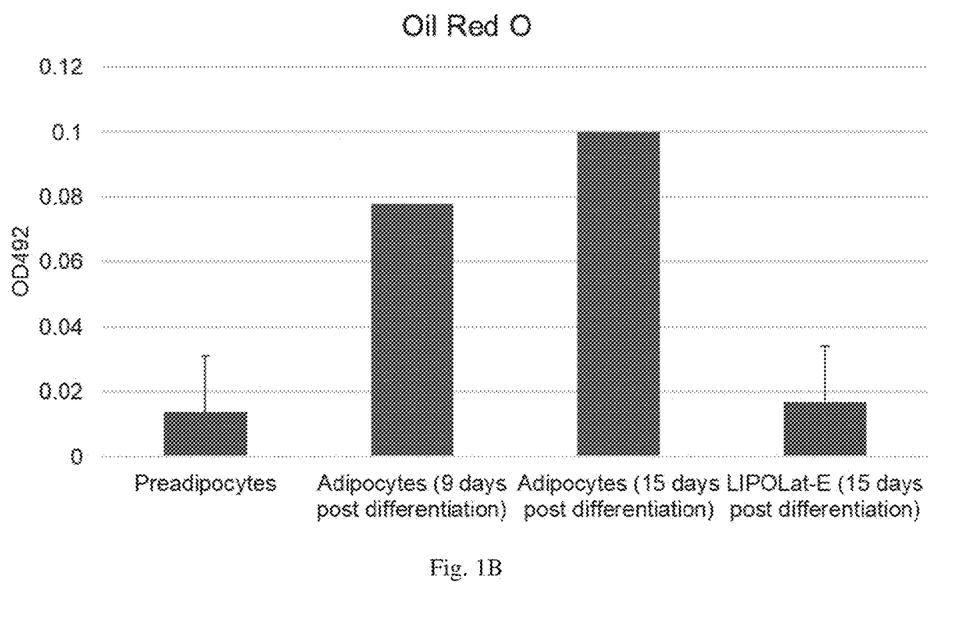
FIG. 1B is a bar graph showing optical density at 492 nm ($OD_{492}$) of the indicated Oil red O-stained preadipocytes, differentiated adipocytes, and differentiated adipocytes treated with an EggPC-latanoprost liposomal composition (LIPOLat-E). Error bars are standard deviation.

After 9 and 15 days, the plated cells were partially and fully differentiated into adipocytes, respectively. Both partially and fully differentiated adipocytes accumulated lipid droplets. At day 15 after plating, the adipocytes were treated with vehicle or with latanoprost encapsulated in EggPC liposomes (EggPC-latanoprost; equivalent of 10 μg/mL latanoprost) for 24 h. The presence of lipids was observed by light microscopy after Oil red O staining and quantified by measuring absorbance at 492 nm. The results are shown in FIGS. 1A and 1B, respectively.

Treatment of adipocytes with EggPC-latanoprost reduced the amount of lipid stored in lipid droplets by 5-fold, as compared to vehicle-treated cells.

Figure 2A:
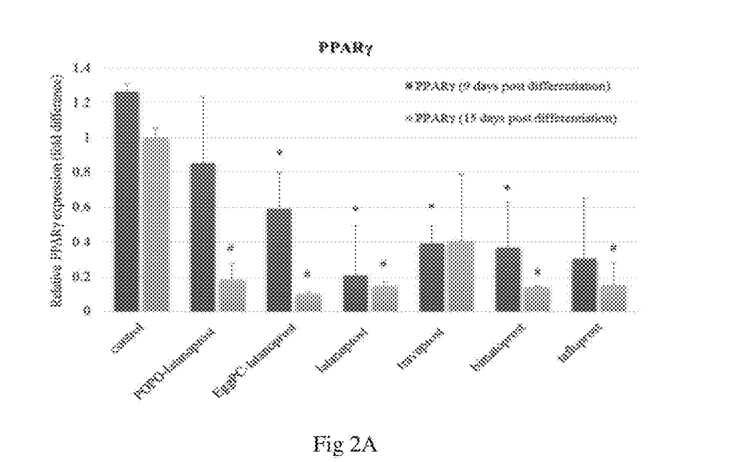
FIG. 2A is a bar graph showing relative mRNA expression of peroxisome proliferator-activated receptor gamma (PPAR-y) in adipocytes differentiated from preadipocytes in culture for 9 days (dark bars) or 15 days (light bars) treated with vehicle (control) or treated with the indicated formulation. *$p<0.05$ vs. control (9 days post differentiation) group; #$p<0.05$ control (15 days post differentiation) group.
Figure 2B:
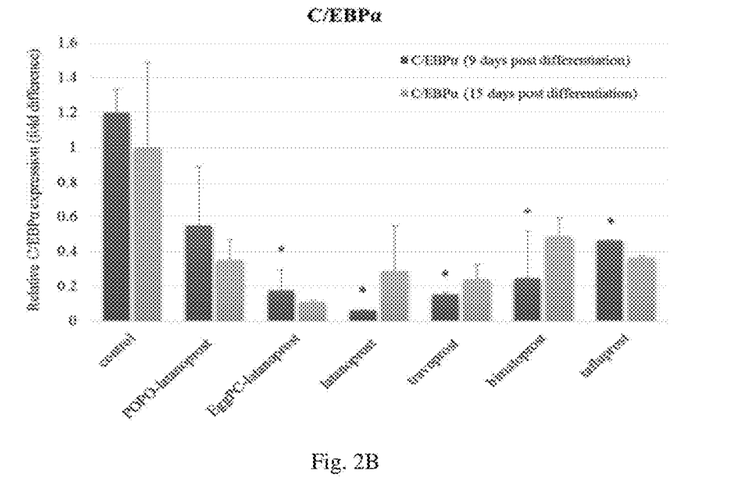
FIG. 2B is a bar graph showing relative mRNA expression of CCAAT-enhancer-binding protein α (C/EBPα) in adipocytes differentiated from preadipocytes in culture for 9 days (dark bars) or 15 days (light bars) treated with vehicle (control) or treated with the indicated formulation. *$p<0.05$ vs. control (9 days post differentiation) group.
Figure 2C:
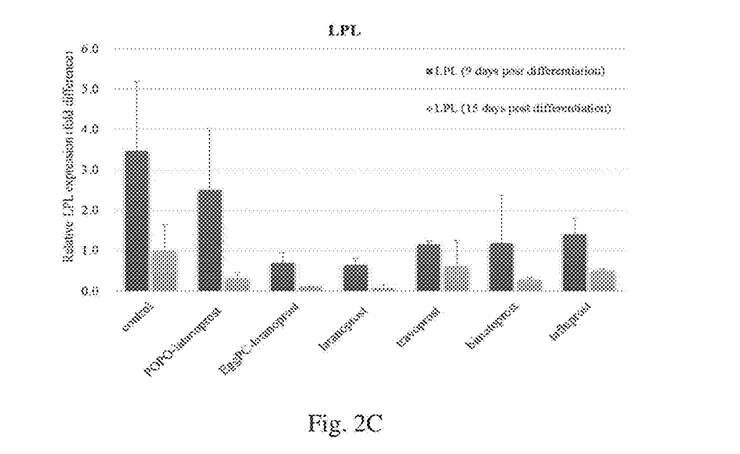
FIG. 2C is a bar graph showing relative mRNA expression of lipoprotein lipase (LPL) in adipocytes differentiated from preadipocytes in culture for 9 days (dark bars) or 15 days (light bars) treated with vehicle (control) or treated with the indicated formulation.

Gene expression in the treated and untreated adipocytes was examined by quantitative real-time PCR analysis. Total RNA from adipocytes was isolated using the RNAzol® RT reagent (Molecular Research Center, Inc., Cincinnati, Ohio, USA) and reverse-transcribed using the QuantiTect reverse transcription kit (Qiagen Inc., Chatsworth, Calif., USA) according to the supplier's instructions. Messenger RNA expression of adipogenesis-promoting genes C/EBPα, PPARγ, and LPL were determined by quantitative analysis of real-time PCR (RT-PCR) using FastStart Universal SYBR Green Master Mix (Roche Applied Science) in a LightCycler® 480 Real-Time PCR System (Roche Applied Science, Germany). Thermal cycler conditions were 95° C. for 10 min. followed by 55 cycles (10 s at 95° C.; 5 s at 50° C. and 13 s at 72° C.). All samples were tested in duplicate and relative mRNA expression calculated by the $\Delta\Delta C_t$ method and normalized to expression of a housekeeping gene. The results are shown in FIGS. 2A-2C.

EggPC-latanoprost, POPC-latanoprost, and free latanoprost each suppressed expression of the adipocyte-promoting genes C/EBPα, PPARγ, and LPL.

Example 2: In Vivo Fat Reduction

The ability of liposome-encapsulated latanoprost to reduce fat deposits in vivo was tested by direct injection into inguinal fat pads of mice.

Figure 3:
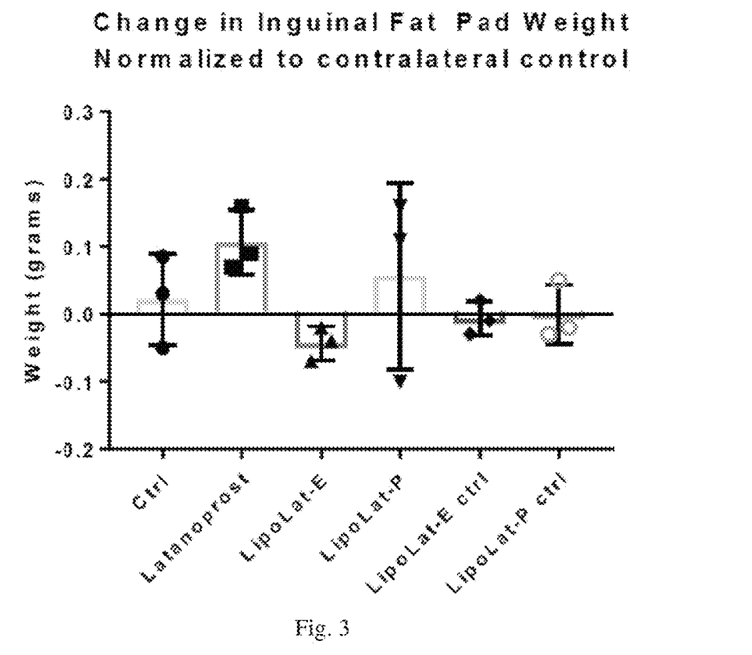
FIG. 3 is a bar graph showing change in weight of inguinal fat pad injected with phosphate-buffered saline (PBS; CTRL), latanoprost, EggPC-latanoprost liposomal composition (LIPOLat-E), POPC-latanoprost liposomal composition (LIPOLat-P), unloaded EggPC liposomes (LipoLat-E ctrl), and unloaded POPC liposomes (LipoLat-P ctrl) normalized to contralateral non-injected fat pad.
Figure 4A:
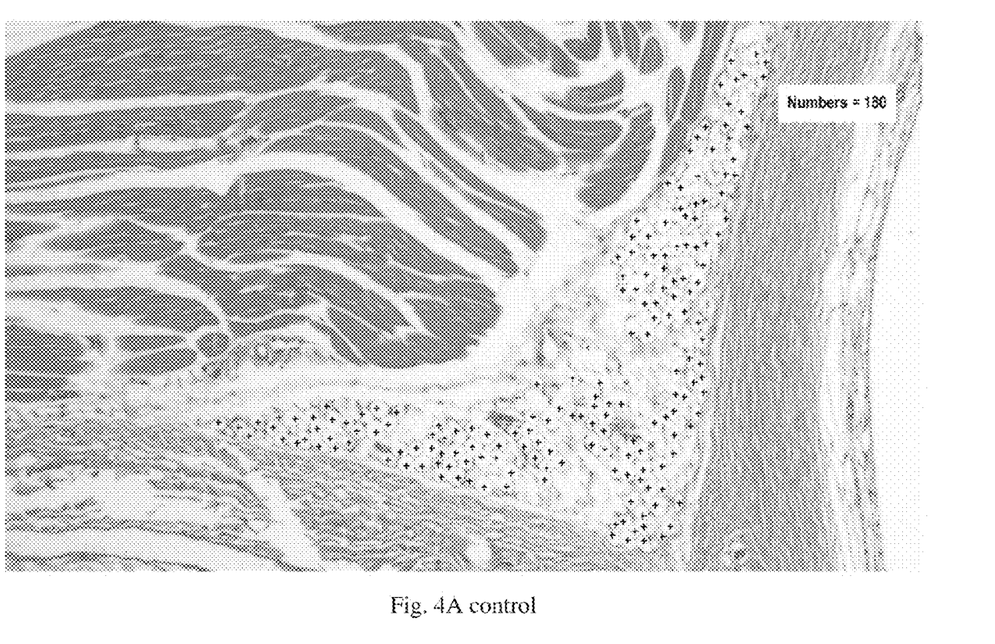
FIG. 4A is a light micrograph at 4× magnification of a section through the orbital region of an untreated rat eye. Adipocytes are marked with a + symbol.
Figure 4B:
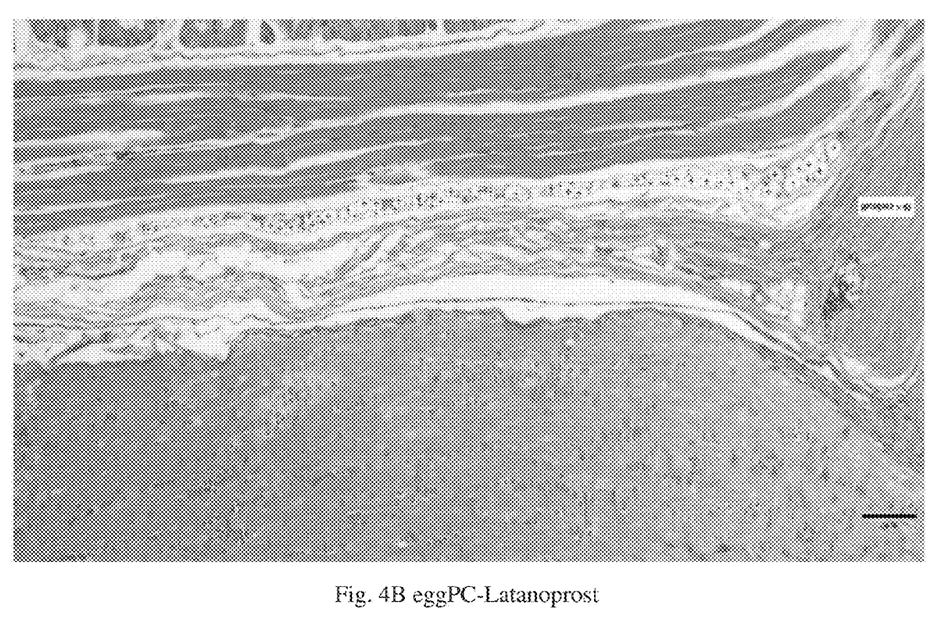
FIG. 4B is a light micrograph at 4× magnification of a section through the orbital region of a rat eye (contralateral to the eye shown in FIG. 4A) 7 days after retrobulbar injection of an EggPC-latanoprost formulation. Adipocytes are marked with a + symbol.
Figure 4C:
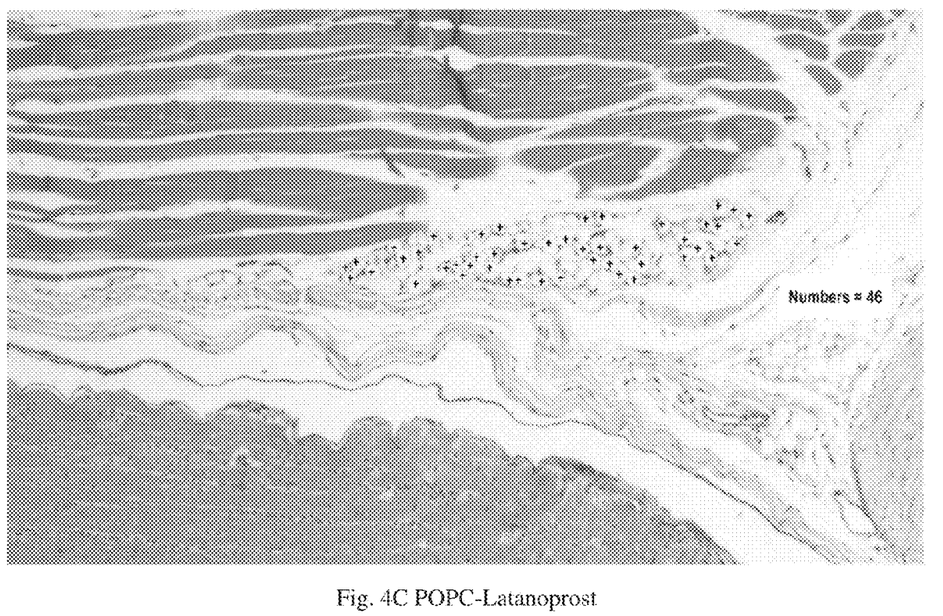
FIG. 4C is a light micrograph at 4× magnification of a section through the orbital region of a rat eye 7 days after retrobulbar injection of a POPC-latanoprost formulation. Adipocytes are marked with a + symbol.
Figure 4D:
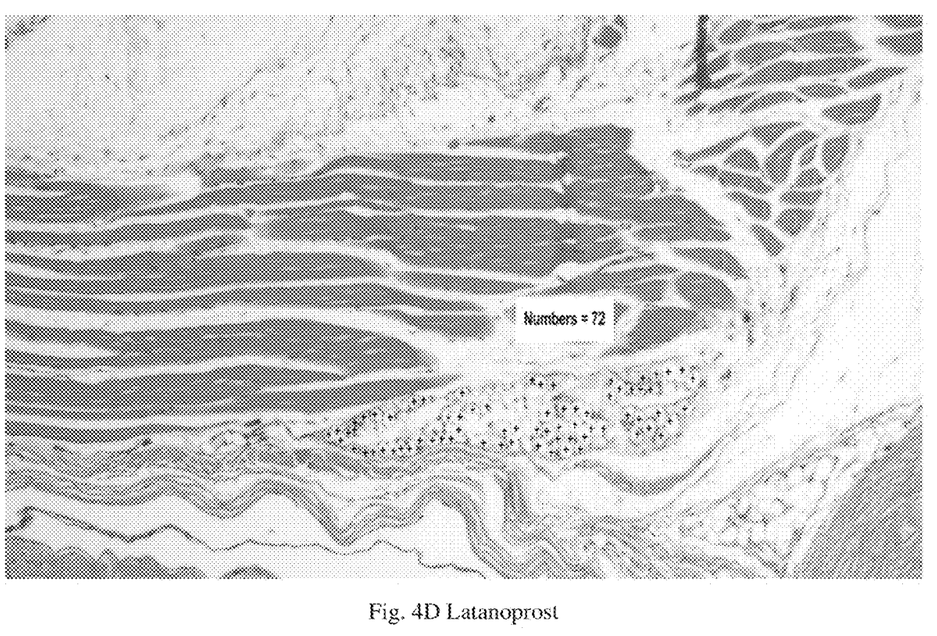
FIG. 4D is a light micrograph at 4× magnification of a section through the orbital region of a rat eye 7 days after retrobulbar injection of free latanoprost. Adipocytes are marked with a + symbol.
Figure 4E:
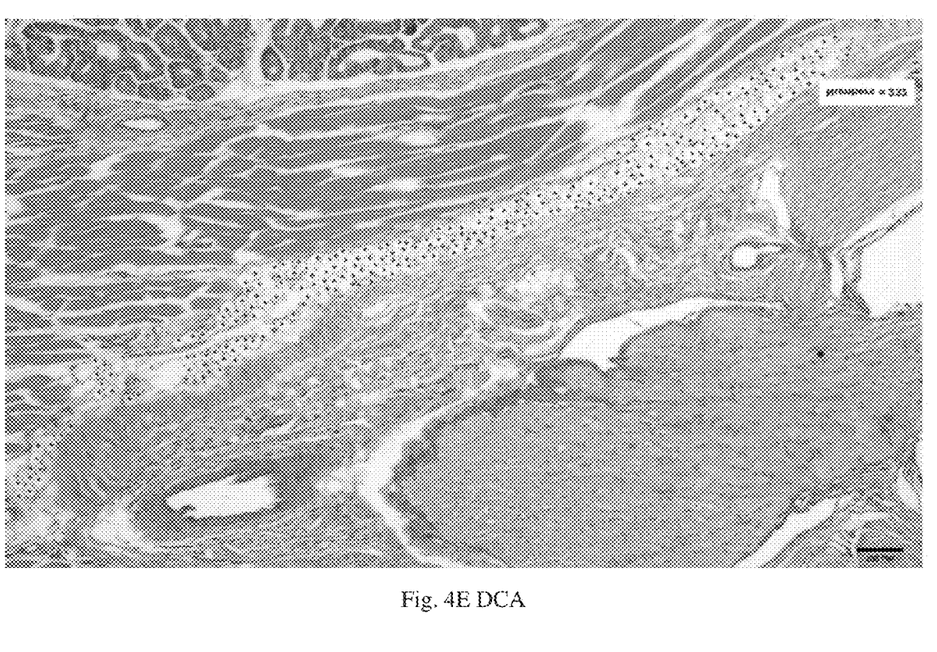
FIG. 4E is a light micrograph at 4× magnification of a section through the orbital region of a rat eye 7 days after retrobulbar injection of deoxycholic acid (DCA). Adipocytes are marked with a + symbol.
Figure 4F:
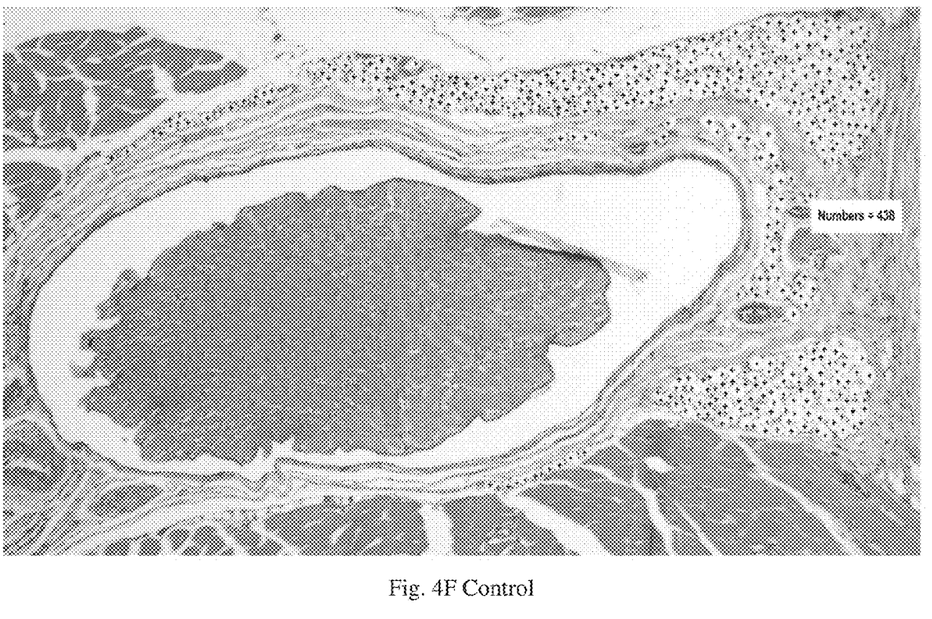
FIG. 4F is a light micrograph at 4× magnification of a section through the orbital region of an untreated rat eye (contralateral to the eye shown in FIG. 4E). Adipocytes are marked with a + symbol.

Each of three animals were injected into one inguinal fat pad with 100 μL of vehicle, 100 μL containing 100 μg latanoprost, 100 μL of EggPC-latanoprost containing 100 μg latanoprost, or 100 μL of POPC-latanoprost containing 100 μg latanoprost. Seven days later, the mice were sacrificed and the weights of both the injected inguinal fat pad and the contralateral un-injected fat pad were measured. The results are shown in FIG. 3.

A single injection of free latanoprost did not result in any weight reduction in the injected inguinal fat pad after 7 days, as compared to the un-injected contralateral inguinal fat pad. Indeed, there was an increase in fat pad weight after latanoprost injection.

Surprisingly, injection of EggPC-latanoprost significantly reduced the weight of the injected inguinal fat pad by 9% at 7 days post-injection, as compared to the un-injected fat pad.

Example 3: Short-Term Reduction in Adipocyte Counts in Eye Orbit Intraconal Region Free latanoprost, EggPC-latanoprost, and POPC-latanoprost were each introduced by retrobulbar injection into the orbit of the rat eye to ascertain its effect on intraconal fat deposits. As a positive control, deoxycholic acid (DCA; KYBELLA®) was also injected. DCA has been approved by the United States Food and Drug Administration for reducing fat cells in the chin.

Six rats were injected in a single eye for each of treatment. The contralateral eye of each animal was not injected, thus serving as a negative control. Drug dosing and injection volumes for each group of animals are shown in Table 1 below.

TABLE 1

Experimental groups

| Group | Drug Dose (μg/eye/dose) | Drug Concentration (mg/mL) | Dose Volume (μL/eye/dose) |
|---|---|---|---|
| A: EggPC-latanoprost | 25 | 1 | 25 |
| B: POPC-latanoprost | 25 | 1 | 25 |
| C: latanoprost | 25 | 0.05 | 500 |
| D: DCA | 2000 | 10 | 200 |

The number of adipocytes present in the intraconal fat deposit at day 7 post-injection was counted by computer analysis of histopathology images and compared to the number of adipocytes in the contralateral un-injected eye. The results are shown in FIGS. 4A-4F and in Table 2 below.

TABLE 2

Reduction in adipocyte number

| Treatment | Adipocyte cell count reduction[a] |
|---|---|
| EggPC-latanoprost | 83.58% |
| POPC-latanoprost | 69.64% |
| latanoprost | 56.52% |
| DCA | 39.04% |

[a]Percent reduction in total adipocyte number in intraconal fat deposit as compared to adipocyte number in intraconal fat deposit of contralateral un-injected eye The results showed that injection of EggPC-latanoprost and POPC-latanoprost were most effective at reducing adipocyte numbers after a single injection.

Example 4: Retrobulbar Injection into Orbital Fat in Rat Model

Materials

Free latanoprost, EggPC-latanoprost, POPC-latanoprost, and DCA were each introduced by retrobulbar injection into the orbit of the rat eye to ascertain its effect on intraconal fat deposits over a three-week period.

EggPC-latanoprost and POPC-latanoprost were prepared as sterile solutions containing 1 mg/mL of latanoprost and 0.5 mL of each solution was stored in a vial at 2-8° C.

XALATAN® is a clear, isotonic, buffered, preserved colorless solution of latanoprost (50 µg/mL). It was supplied as 2.5 mL of solution in a 5 mL clear bottle and stored at 2° to 8° C.

KYBELLA® (DCA) was obtained as a 10 mg/mL sterile solution in a 2 mL vial and stored at 20-25° C.

The test drugs were warmed at room temperature for a minimum of 30 minutes prior to use. Dosing syringes were filled directly from the storage vials using aseptic technique.

Experimental Protocol

Twenty-four male Lewis rats (*Rattus norvegicus*) at 8-10 weeks of age were used in the study. Their weights at the start of the study ranged from 250-300 g.

Six rats were assigned to each of four groups at least one day prior to drug dosing using a selection designed to achieve similar group mean body weights. The four groups were treated as those in Example 3 and are shown in Table 1 above. Animals in Groups A-D were weighed prior to injection and weekly thereafter.

Rats were anesthetized and a 30-gauge needle was used to inject the drugs into the retrobulbar space of the right orbit of each animal. The left orbit served as a contra-lateral control. All rats awoke from anesthesia without complication.

Intraocular pressure (TOP) measurements were taken pre- and 3-week post-injection of each eye of all 24 rats.

On Day 21, 3 weeks after injection, rats were euthanized by cardiac perfusion with 4% paraformaldehyde. After perfusion, each rat was decapitated and the head was placed in a 10% formalin solution for 2 days. Each orbit was carefully exenterated subperiosteally with a scalpel and placed back in 10% formalin solution for 1 day (6 orbits from 3 animals per group) and the remaining orbits were placed back in a 10% formalin solution for 2 weeks. Exenterated orbits were embedded in paraffin and cut into 5 µm sections. Sections centered around the intraconal fat and optic nerve were stained with hematoxylin-eosin for histologic examination by a trained ocular pathologist and a second observer in a blinded fashion.

Sample Analysis

Sections were examined histologically for optic nerve injury, atrophy of orbital fat, adipocyte density, and cytotoxicity evidenced by, e.g., adipocytolysis, blood vessel injury and repair, neutrophilic inflammation, lysis of locally present neutrophils, hemorrhage, lipid lake formation, and neovascularization.

The intraconal fat of the orbital sections were examined under light microscopy and images scanned for further analysis. The areas of intraconal orbital fat were cropped and the adipocytes counted using ImageJ software (Rasband W.S., US National Institutes of Health, Bethesda, Md.) to determine adipocyte density using a previously described method. See Park et al., 2011, Jpn. J. Ophthalmol. 55:22-27. The density of adipocytes in the intraconal orbital fat area was calculated and compared between groups via a 2-tailed Student t test.

Adipocyte size heterogeneity was analyzed in the cropped images of the intraconal fat light using a maximally stable extremal regions-based segmentation algorithm implemented in MATLAB (Mathworks, Natick, Mass.). A maximally stable extremal region algorithm entitled VL_FEAT was used to find extremal regions with parameters of delta=1, maximum variation=0.2, minimum diversity=0.5. Maximally stable extremal region-determined regions with sizes less than 10 pixels or eccentricity larger than 0.9 was discarded as false positives. The mean segmented adipocyte size for each image was calculated and the groups were compared using Student t test.

Results

Figure 5A:
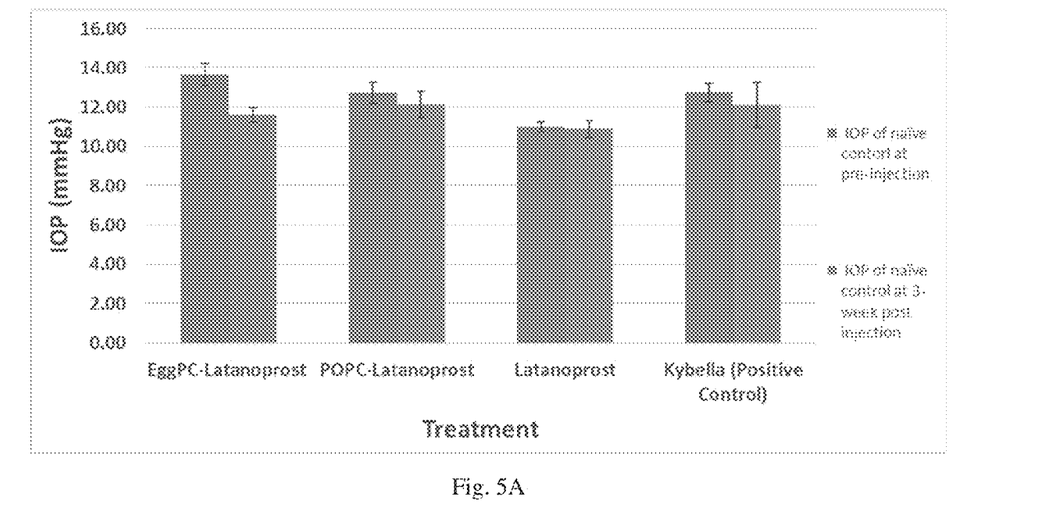
FIG. 5A is a bar graph showing intraocular pressure (TOP) in un-injected eyes of rats in which the contralateral eye was treated with the indicated formulation by retrobulbar injection. IPO was measured pre-injection (first bar in each pair) and at 3 weeks post-injection (second bar in each pair).
Figure 5B:
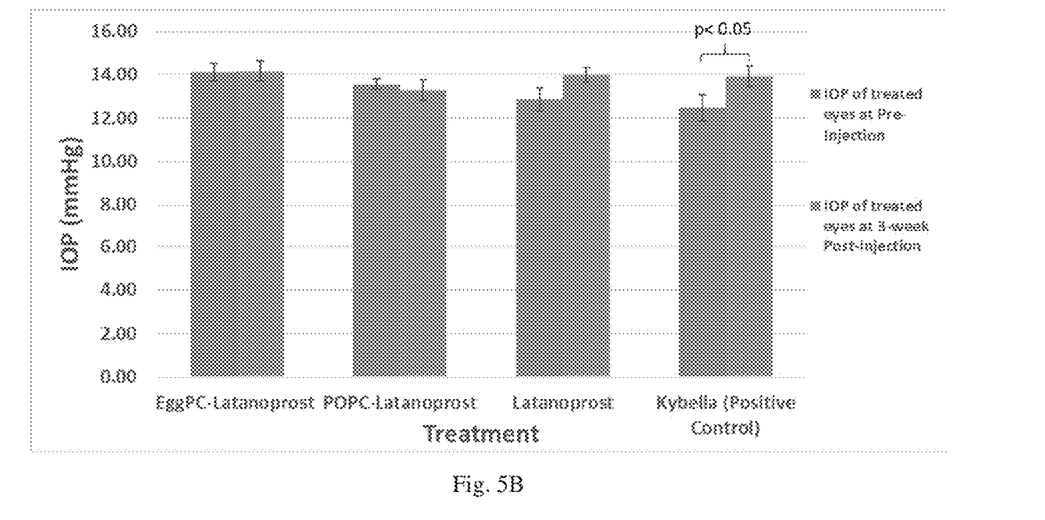
FIG. 5B is a bar graph showing intraocular pressure (TOP) of rats in which the eye was treated with the indicated formulation by retrobulbar injection. IPO was measured pre-injection (first bar in each pair) and at 3 weeks post-injection (second bar in each pair).

IOP remained stable in naïve (un-injected) control eyes, with no significant change in IOP during the three-week experimental protocol. See FIG. 5A. IOP in eyes following retrobulbar injection of EggPC-latanoprost, POPC-latanoprost, and latanoprost also remained stable for three weeks. See FIG. 5B. IOP in rats injected with DCA showed a significant increase in IOP. See Id.

Quantitative image analysis showed significant increases in the area of the retrobulbar fat complex after injection of POPC-latanoprost, latanoprost, and DCA but not after injection of EggPC-latanoprost. See Table 3 below.

TABLE 3

Area of Retrobulbar Fat complex (mm$^2$)

| Groups | Treated Eyes Mean ± SEM (n = 6) | Naïve Control Eyes Mean ± SEM (n = 6) | p | Percentage Increase |
|---|---|---|---|---|
| EggPC-L | 0.117 ± 0.089 | 0.044 ± 0.024 | >0.05 | 165% |
| POPC-L | 0.145 ± 0.084 | 0.041 ± 0.024 | <0.05 | 252% |
| latanoprost | 0.131 ± 0.089 | 0.034 ± 0.007 | <0.05 | 283% |
| DCA | 0.167 ± 0.093 | 0.054 ± 0.027 | <0.05 | 208% |

Not to be bound by theory, it is believed that the increase in area of the retrobulbar fat complex results from an increase in volume of extra-ocular muscles coupled with a reduction in fat cells, fibroblasts, or T cells. Differential changes in area upon injection of different formulations might result from remodeling of muscle and fat tissue occurring at distinct rates.

Quantitative image analyses also revealed significant increases in the density of adipocytes of all injected eyes. The results are shown below in Table 4.

TABLE 4

Mean Density of Adipocytes (cells/mm³)

| Groups | Treated Eyes Mean ± SEM (n = 6) | Naïve Control Eyes Mean ± SEM (n = 6) | p | Percent Increase |
|---|---|---|---|---|
| EggPC-L | 8155.73 ± 684.86 | 5179.35 ± 765.77 | <0.01 | 43% |
| POPC-L | 8121.36 ± 856.83 | 4947.70 ± 1249.14 | <0.01 | 64% |
| latanoprost | 8574.68 ± 1456.73 | 5433.75 ± 455.87 | <0.01 | 58% |
| DCA | 7606.21 ± 754.39 | 5623.71 ± 357.69 | <0.01 | 35% |

Among the 4 test groups, the group injected with POPC-latanoprost demonstrated the highest percent increase (64%).

Absolute adipocyte counts were also obtained by image analysis. The results are shown in Table 5 below.

TABLE 5

Adipocyte Cell Counts

| Groups | Treated Eyes Mean ± SEM (n = 6) | Naïve Control Eyes Mean ± SEM (n = 6) | $p^a$ | Percentage Decrease |
|---|---|---|---|---|
| EggPC-L | 138 ± 103 | 280 ± 7 | <0.01 | 51% |
| POPC-L | 92 ± 44 | 290 ± 8 | <0.01 | 68% |
| latanoprost | 108 ± 52 | 281 ± 8 | <0.01 | 61% |
| DCA | 179 ± 47 | 285 ± 10 | <0.01 | 37% |

$^a$Comparison of treated versus untreated by Student's t-test

POPC-latanoprost injection induced the largest decrease (68%) of adipocyte cell counts, as compared to any other tested treatment.

Further statistical analysis revealed that the reduction in adipocytes induced by POPC-Latanprost was significantly different from the reduction induced by any other treatment. See Table 6 below.

TABLE 6

Significance between groups in adipocyte numbers

| P-Value | EggPC-L | POPC-L | latanoprost | DCA |
|---|---|---|---|---|
| EggPC-L | | 6.72275E-05 | 0.00941 | 0.008317997 |
| POPC-L | | | 0.000426 | 1.36184E-07 |
| latanoprost | | | | 1.13807E-05 |
| DCA | | | | |

Figure 6A:
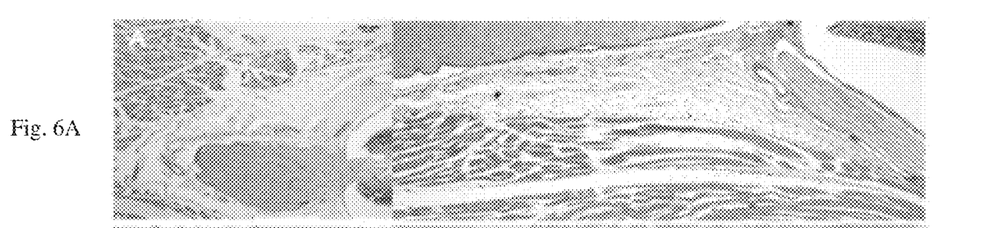
FIG. 6A is a light micrograph of a section through the orbital region of a rat eye 21 days after retrobulbar injection of EggPC-latanoprost. Left-hand panel shows 1× magnification and right-hand panel shows 4× magnification.
Figure 6B:
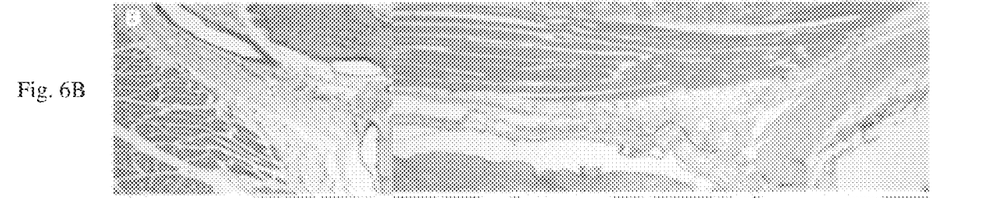
FIG. 6B is a light micrograph of a section through the orbital region of a rat eye 21 days after retrobulbar injection of POPC-latanoprost. Left- and right-hand panel magnifications are as above.
Figure 6C:
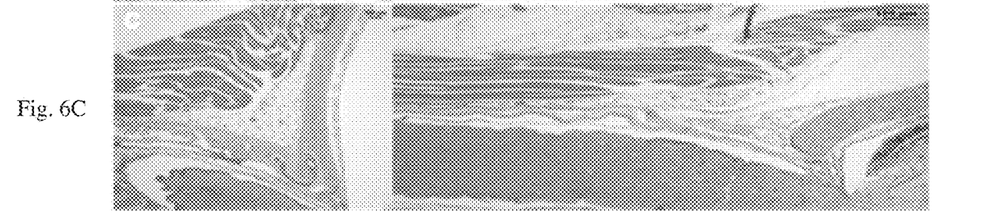
FIG. 6C is a light micrograph of a section through the orbital region of a rat eye 21 days after retrobulbar injection of latanoprost. Left- and right-hand panel magnifications are as above.
Figure 6D:
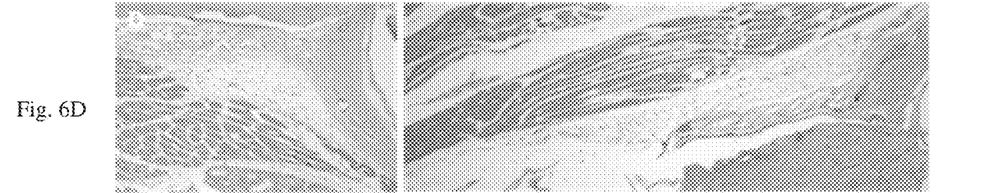
FIG. 6D is a light micrograph of a section through the orbital region of a rat eye 21 days after retrobulbar injection of Deoxycholic acid. Left- and right-hand panel magnifications are as above.
Figure 6E:
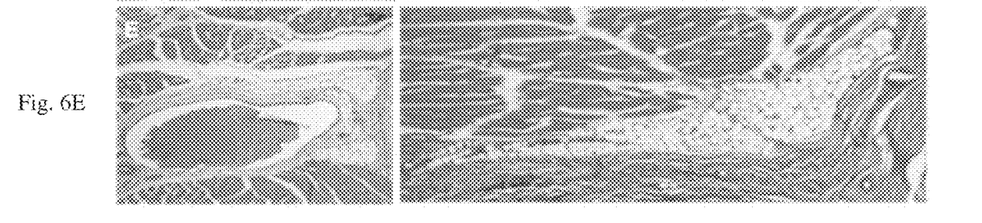
FIG. 6E is a light micrograph of a section through an un-injected eye. Left- and right-hand panel magnifications are as above.

Histopathologic evaluation of the orbit tissues revealed no inflammatory cell infiltrate in either the injected orbits or the naïve controls. Qualitative light microscopy analysis showed that orbital fat appeared undisturbed in the naïve control specimens. See FIG. 6E.

By contrast, small, irregularly-shaped, fragmented adipocytes with high adipocyte density per unit area were seen in injected eyes. See FIGS. 6A-6D. This observation suggested the atrophy of the intraconal fat.

Figure 7A:
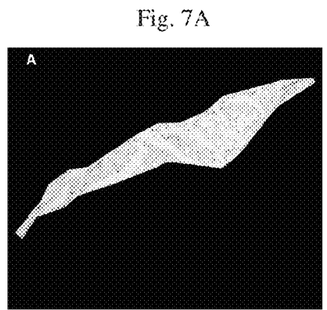
FIG. 7A is a computer-generated cropped image of the image shown in FIG. 6A, delineating areas of orbital fat and identifying individual adipocytes.
Figure 7B:
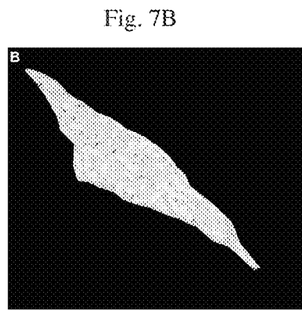
FIG. 7B is a computer-generated cropped image of the image shown in FIG. 6B, delineating areas of orbital fat and identifying individual adipocytes.
Figure 7C:
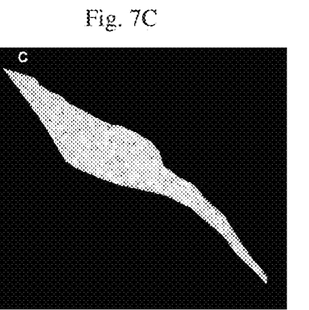
FIG. 7C is a computer-generated cropped image of the image shown in FIG. 6C, delineating areas of orbital fat and identifying individual adipocytes.
Figure 7D:
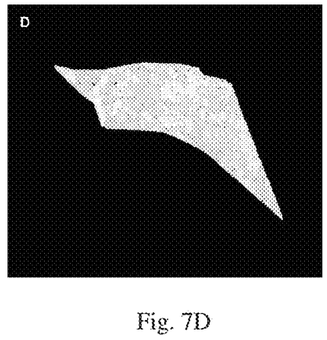
FIG. 7D is a computer-generated cropped image of the image shown in FIG. 6D, delineating areas of orbital fat and identifying individual adipocytes.
Figure 7E:
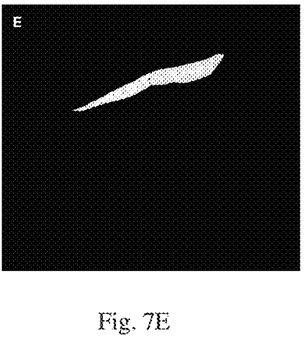
FIG. 7E is a computer-generated cropped image of the image shown in FIG. 6E, delineating areas of orbital fat and identifying individual adipocytes.

Computer-aided morphological analyses on those specimens from injected eyes demonstrated atrophy of orbital fat with significantly increased adipocyte density and heterogeneity in the intraconal space (see FIGS. 7A-7D) when compared with naïve controls (see, e.g., FIG. 7E).

In sum, orbital injection of EggPC-latanoprost, POPC-latanoprost, latanoprost, and DCA resulted in more heterogeneity among adipocytes that were densely packed in the intraconal space, as compared to naïve contra-lateral control orbits. It was is unexpected that in the 7-day study (Example 3), EggPC-latanoprost was much more effective than POPC-latanoprost for reducing adipocyte numbers, yet the 21-day study (Example 4) revealed the opposite result that POPC-latanoprost was more effective than EggPC-latanoprost, despite the similarities between these two encapsulated forms of latanoprost.

Example 5: Clinical Trial for Steatoblepharon Management

Twenty subjects at a single center are recruited. Each subject has a clinically significant lower eyelid steatoblepharon, i.e., eyebag.

A single injection of 120-240 μg of POPC-latanoprost (1 mg/ml latanoprost) is made into the lower eyelid of the more severe eye. The less severe eyelid is injected with the same volume of solution having the same composition lacking the latanoprost.

The safety and tolerability of POPC-latanoprost injection into the lower eyelid is analyzed over a 12-week period. The pharmacokinetics of POPC-latanoprost is also measured during the same period.

OTHER EMBODIMENTS

All of the features disclosed in this specification may be combined in any combination. Each feature disclosed in this specification may be replaced by an alternative feature serving the same, equivalent, or similar purpose. Unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for reducing a fat deposit in vivo, the method comprising contacting the fat deposit with an effective amount of a composition of latanoprost encapsulated in a liposome, wherein the liposome is formed solely of egg phosphatidylcholine or palmitoyloleoyl phosphatidylcholine, the fat deposit is a subcutaneous fat deposit or a visceral fat deposit, the contacting step is carried out by direct injection of the composition into the fat deposit, a concentration of latanoprost in the composition is 0.5 mg/mL to 3.0 mg/mL, and the effective amount of the composition reduces a number of adipocytes in the fat deposit by 5% to 90%.

2. The method of claim 1, wherein the number of adipocytes in the fat deposit is reduced by 10% to 90%.

3. The method of claim 2, wherein the number of adipocytes in the fat deposit is reduced by 35% to 90%.

4. The method of claim 1, wherein the concentration of latanoprost is 1.0 mg/mL to 2.3 mg/mL.

5. The method of claim 1, wherein a volume of 25 μL to 75 μl of the composition is injected for each 0.5 cm³ to 1.0 cm³ of the fat deposit.

6. A method for reducing a fat deposit in vivo, the method comprising injecting into an interstitial space adjacent to the fat deposit an effective amount of a composition of latanoprost encapsulated in a liposome, wherein the liposome is formed solely of egg phosphatidylcholine or palmitoyloleoyl phosphatidylcholine, the fat deposit is a subcutaneous fat deposit or a visceral fat deposit, and the effective amount of the composition reduces a number of adipocytes in the fat deposit by 5% to 90%.

7. The method of claim 6, wherein a concentration of latanoprost in the composition is 0.5 mg/mL to 3.0 mg/mL.

8. The method of claim 7, wherein the concentration of latanoprost is 1.0 mg/mL to 2.3 mg/mL.

9. The method of claim 6, wherein a volume of 25 µL to 75 µl of the composition is injected for each 0.5 cm$^3$ to 1.0 cm$^3$ of the fat deposit.

10. A method for reducing a subcutaneous fat deposit in vivo, the method comprising injecting into or adjacent to the subcutaneous fat deposit an effective amount of a composition of latanoprost encapsulated in a liposome, wherein the liposome is formed solely of egg phosphatidylcholine or palmitoyloleoyl phosphatidylcholine, a concentration of latanoprost in the composition is 0.5 mg/mL to 3.0 mg/mL, and the effective amount of the composition reduces a number of adipocytes in the subcutaneous fat deposit by 5% to 90%.

11. The method of claim 10, wherein the concentration of latanoprost is 1.0 mg/mL to 2.3 mg/mL.

12. The method of claim 10, wherein a volume of 25 µL to 75 µl of the composition is injected for each 0.5 cm$^3$ to 1.0 cm$^3$ of the subcutaneous fat deposit.

13. A method for treating steatoblepharon in a subject, the method comprising identifying a subject in need of treatment for steatoblepharon and injecting into a fat deposit in an eyelid of the subject an effective amount of a composition of latanoprost encapsulated in a liposome, wherein the liposome is formed solely of egg phosphatidylcholine or palmitoyloleoyl phosphatidylcholine, a concentration of latanoprost in the composition is 0.5 mg/mL to 3.0 mg/mL, and the effective amount of the composition reduces a number of adipocytes in the fat deposit by 5% to 90%.

14. The method of claim 13, wherein the number of adipocytes in the fat deposit is reduced by 10% to 90%.

15. The method of claim 14, wherein the number of adipocytes in the fat deposit is reduced by 35% to 90%.

16. The method of claim 13, wherein the concentration of latanoprost is 1.0 mg/mL to 2.3 mg/mL.

17. The method of claim 13, wherein a volume of 25 µL to 75 µl of the composition is injected for each 0.5 cm$^3$ to 1.0 cm$^3$ of the fat deposit.

18. A method for treating proptosis in a subject, the method comprising identifying a subject in need of treatment for proptosis and injecting into an intraconal space of the subject an effective amount of a composition of latanoprost encapsulated in a liposome, wherein the liposome is formed solely of egg phosphatidylcholine or palmitoyloleoyl phosphatidylcholine, a concentration of latanoprost in the composition is 0.5 mg/mL to 3.0 mg/mL, and the effective amount of the composition reduces a number of adipocytes in the intraconal space by at least 35%.

19. The method of claim 18, wherein the proptosis is a result of thyroid-associated orbitopathy.

20. The method of claim 19, wherein the concentration of latanoprost is 1.0 mg/mL to 2.3 mg/mL.

21. The method of claim 18, wherein the subject suffers from Grave's disease or Hashimoto's thyroiditis.

22. The method of claim 21, wherein the concentration of latanoprost is 1.0 mg/mL to 2.3 mg/mL.

23. A method for treating obstructive sleep apnea associated with an excess upper airway fat in a subject, the method comprising identifying a subject in need of treatment for obstructive sleep apnea and injecting into an upper airway fat deposit of the subject an effective amount of a composition of latanoprost encapsulated in a liposome, wherein the liposome is formed solely of egg phosphatidylcholine or palmitoyloleoyl phosphatidylcholine, a concentration of latanoprost in the composition is 0.5 mg/mL to 3.0 mg/mL, and the effective amount of the composition reduces a number of adipocytes in the upper airway fat deposit by 5% to 90%.

24. The method of claim 23, wherein the upper airway fat deposit is located in the palate, the tongue, or the pharynx.

25. The method of claim 23, wherein the concentration of latanoprost is 1.0 mg/mL to 2.3 mg/mL.

26. The method of claim 23, wherein the number of adipocytes in the fat deposit is reduced by 10% to 90%.

27. The method of claim 26, wherein the number of adipocytes in the fat deposit is reduced by 35% to 90%.

\* \* \* \* \*